United States Patent
Tanner et al.

(10) Patent No.: US 10,285,926 B2
(45) Date of Patent: May 14, 2019

(54) SUPERABSORBENT POLYMERS AND STARCH POWDERS FOR USE IN SKIN CARE COMPOSITIONS

(71) Applicant: The Procter & Gamble Company, Cincinnati, OH (US)

(72) Inventors: Paul Robert Tanner, Lebanon, OH (US); Mridula Manohar, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/196,384

(22) Filed: Jun. 29, 2016

(65) Prior Publication Data

US 2016/0374933 A1 Dec. 29, 2016

Related U.S. Application Data

(60) Provisional application No. 62/186,199, filed on Jun. 29, 2015.

(51) Int. Cl.

| | |
|---|---|
| *A61K 8/06* | (2006.01) |
| *A61K 8/73* | (2006.01) |
| *A61K 8/81* | (2006.01) |
| *A61K 8/92* | (2006.01) |
| *A61Q 5/00* | (2006.01) |
| *A61Q 15/00* | (2006.01) |
| *A61Q 17/04* | (2006.01) |
| *A61Q 19/00* | (2006.01) |
| *A61Q 19/02* | (2006.01) |
| *A61Q 19/04* | (2006.01) |
| *A61Q 19/06* | (2006.01) |
| *A61Q 19/08* | (2006.01) |

(52) U.S. Cl.
CPC ............... *A61K 8/92* (2013.01); *A61K 8/062* (2013.01); *A61K 8/732* (2013.01); *A61K 8/8147* (2013.01); *A61Q 5/006* (2013.01); *A61Q 15/00* (2013.01); *A61Q 17/04* (2013.01); *A61Q 19/00* (2013.01); *A61Q 19/007* (2013.01); *A61Q 19/02* (2013.01); *A61Q 19/04* (2013.01); *A61Q 19/06* (2013.01); *A61Q 19/08* (2013.01); *A61K 2800/48* (2013.01)

(58) Field of Classification Search
CPC .. A61K 2800/48; A61K 8/732; A61K 8/8147; A61K 8/92; A61K 8/062; A61Q 15/00; A61Q 17/04; A61Q 19/007; A61Q 19/02; A61Q 19/04; A61Q 19/06; A61Q 19/08; A61Q 5/006; A61Q 19/00
See application file for complete search history.

(56) References Cited

U.S. PATENT DOCUMENTS

| | | |
|---|---|---|
| 3,755,560 A | 8/1973 | Dickert et al. |
| 4,217,344 A | 8/1980 | Vanlerberghe et al. |
| 4,421,769 A | 12/1983 | Dixon et al. |
| 5,030,544 A | 7/1991 | Olbrechts et al. |
| 5,159,485 A | 10/1992 | Nelson |
| 5,223,250 A | 6/1993 | Mitchell et al. |
| 5,236,986 A | 8/1993 | Sakuta |
| 5,254,331 A | 10/1993 | Mausner |
| 5,310,632 A | 5/1994 | Oppenheimer |
| 5,387,417 A | 2/1995 | Rentsch |
| 5,412,004 A | 5/1995 | Tachibana et al. |
| 5,455,048 A | 10/1995 | Lahmani et al. |
| 5,599,555 A | 2/1997 | El-Nokaly |
| 5,654,389 A | 8/1997 | Raleigh |
| 5,688,959 A | 11/1997 | Olbrechts et al. |
| 5,733,531 A | 3/1998 | Mitchnick et al. |
| 5,759,526 A | 6/1998 | Simonnet et al. |
| 5,780,060 A | 7/1998 | Levy et al. |
| 5,811,487 A | 9/1998 | Schulz, Jr. et al. |
| 5,837,793 A | 11/1998 | Harashima et al. |
| 5,876,699 A | 3/1999 | DiSomma et al. |
| 5,925,364 A | 7/1999 | Ribier et al. |
| 5,993,789 A | 11/1999 | Bonda et al. |
| 6,039,935 A | 3/2000 | Mohammadi |
| 6,113,931 A | 9/2000 | Bonda et al. |

(Continued)

FOREIGN PATENT DOCUMENTS

| | | |
|---|---|---|
| CA | 2296625 C | 11/2006 |
| CN | 104893204 A | 9/2015 |

(Continued)

OTHER PUBLICATIONS

U.S. Appl. No. 15/475,519, filed Mar. 31, 2017, Shawn David McConaughy et al.
U.S. Appl. No. 29/576,375, filed Sep. 2, 2016, Lee Burrowes et al.
U.S. Appl. No. 29/576,376, filed Sep. 2, 2016, Lee Burrowes et al.
U.S. Appl. No. 29/636,617, filed Feb. 9, 2018, Lee Burrowes et al.
U.S. Appl. No. 29/621,274, filed Oct. 6, 2017, Angela Rachelle Clark et al.
International Search Report and Written Opinion of the International Searching Authority, PCT/US2009/060401, dated May 12, 2010, 11 pages.

(Continued)

Primary Examiner — Michael B. Pallay
(74) Attorney, Agent, or Firm — John G. Powell

(57) ABSTRACT

A skin care composition is provided that has an oil phase mixture and a water phase. The oil phase mixture has from about 5% to about 30% by weight of the composition, of a wax material and optionally from about 1% to about 20% by weight of the composition, of an oil that is liquid at room temperature. The oil phase mixture has a melting point of about 25° C. to about 50° C. The water phase has from about 0.1% to about 5%, by weight of the composition, of a superabsorbent polymer and from about 20% to about 85% by weight of the composition of water. The composition also has from about 6% to about 30%, by weight of the composition, of particulate material selected from the group consisting of starch particles, silicone elastomer particles and combinations thereof.

33 Claims, No Drawings

(56) References Cited

U.S. PATENT DOCUMENTS

| | | |
|---|---|---|
| 6,126,925 A | 10/2000 | Bonda et al. |
| 6,159,453 A | 12/2000 | Avnir et al. |
| 6,207,782 B1 | 3/2001 | Czech et al. |
| 6,242,099 B1 | 6/2001 | Grandmontagne et al. |
| 6,262,170 B1 | 7/2001 | Kilgour et al. |
| 6,284,916 B1 | 9/2001 | Bonda et al. |
| 6,312,807 B1 | 11/2001 | Ludwig et al. |
| 6,338,838 B1 | 1/2002 | Berset et al. |
| 6,391,288 B1 | 5/2002 | Miyazawa et al. |
| 6,439,440 B1 | 8/2002 | Lasserre |
| 6,472,136 B2 | 10/2002 | Tan et al. |
| 6,482,883 B1 | 11/2002 | Cuch et al. |
| 6,497,891 B2 | 12/2002 | Bara |
| 6,531,117 B2 | 3/2003 | Heger et al. |
| 6,531,160 B2 | 3/2003 | Biatry et al. |
| 6,534,091 B1 | 3/2003 | Garces Garces et al. |
| 6,685,966 B1 | 2/2004 | Dominique et al. |
| 6,733,790 B1 | 5/2004 | Garces Garces |
| 6,814,959 B1 | 11/2004 | Muller et al. |
| 6,818,296 B1 | 11/2004 | Garces Garces et al. |
| 6,827,239 B2 | 12/2004 | Lasserre et al. |
| 6,872,401 B2 | 3/2005 | Seyler et al. |
| 6,955,823 B2 | 10/2005 | Casson et al. |
| 6,979,467 B1 | 12/2005 | Garces Garces et al. |
| 7,357,919 B2 | 4/2008 | Candau |
| 7,713,519 B2 | 5/2010 | Bonda et al. |
| 7,776,350 B2 | 8/2010 | Polonka et al. |
| 7,833,960 B2 | 11/2010 | Lei et al. |
| 8,252,271 B2 | 8/2012 | Singer et al. |
| 9,192,552 B2 | 11/2015 | Tanner et al. |
| 9,271,912 B2 | 3/2016 | Fernandez Prieto et al. |
| 9,549,891 B2 | 1/2017 | Tanner et al. |
| 9,795,552 B2 | 10/2017 | Tanner et al. |
| 9,839,598 B2 | 12/2017 | Tanner et al. |
| 2002/0061321 A1 | 5/2002 | Bara |
| 2002/0131941 A1 | 9/2002 | Habeck et al. |
| 2003/0044469 A1 | 3/2003 | Viladot Petit et al. |
| 2003/0049212 A1 | 3/2003 | Robinson et al. |
| 2003/0064106 A1 | 4/2003 | Garces et al. |
| 2003/0068347 A1 | 4/2003 | Baschong et al. |
| 2003/0108492 A1 | 6/2003 | Chaudhuri |
| 2003/0157035 A1 | 8/2003 | Chaudhuri |
| 2004/0057912 A1 | 3/2004 | Bonda et al. |
| 2004/0057914 A1 | 3/2004 | Bonda et al. |
| 2004/0057916 A1 | 3/2004 | Bonda et al. |
| 2004/0062726 A1 | 4/2004 | Bonda et al. |
| 2004/0121019 A1 | 6/2004 | Perrier et al. |
| 2004/0161468 A1 | 8/2004 | Toumi et al. |
| 2004/0175347 A1 | 9/2004 | Bissett |
| 2004/0228819 A1 | 11/2004 | Rabe et al. |
| 2004/0258644 A1 | 12/2004 | Simonnet |
| 2005/0053561 A1 | 3/2005 | Suginaka |
| 2005/0095210 A1 | 5/2005 | Mattai et al. |
| 2005/0208134 A1 | 9/2005 | Magdassi et al. |
| 2005/0220727 A1 | 10/2005 | Lupia et al. |
| 2006/0013791 A1 | 1/2006 | Shimizu et al. |
| 2006/0034875 A1 | 2/2006 | Nakanishi et al. |
| 2006/0169624 A1 | 8/2006 | Radomyselski et al. |
| 2006/0263309 A1 | 11/2006 | Bissett |
| 2006/0275237 A1 | 12/2006 | Bissett et al. |
| 2006/0292095 A1 | 12/2006 | Biatry et al. |
| 2007/0020220 A1 | 1/2007 | Osborne |
| 2007/0071978 A1 | 3/2007 | Sojka et al. |
| 2007/0078071 A1 | 4/2007 | Lee et al. |
| 2007/0098653 A1 | 5/2007 | Tamasawa et al. |
| 2007/0134481 A1 | 6/2007 | Aubrun-Sonneville |
| 2007/0138672 A1 | 6/2007 | Lee et al. |
| 2007/0160549 A1 | 7/2007 | Hunt et al. |
| 2007/0185038 A1 | 8/2007 | Bissett et al. |
| 2007/0190325 A1 | 8/2007 | Berg-Schultz |
| 2007/0207222 A1 | 9/2007 | Yu et al. |
| 2008/0019930 A1 | 1/2008 | Candau et al. |
| 2008/0031909 A1 | 2/2008 | Van Benthem et al. |
| 2008/0089913 A1 | 4/2008 | Kallmayer et al. |
| 2008/0118568 A1 | 5/2008 | Smets et al. |
| 2008/0139453 A1 | 6/2008 | Yoshimi et al. |
| 2008/0145324 A1 | 6/2008 | Richard et al. |
| 2008/0145436 A1 | 6/2008 | Lorant |
| 2008/0146478 A1 | 6/2008 | Lei et al. |
| 2008/0268050 A1 | 10/2008 | Gerrish et al. |
| 2008/0274149 A1 | 11/2008 | Seiler et al. |
| 2008/0311064 A1 | 12/2008 | Lei et al. |
| 2008/0317788 A1 | 12/2008 | Louzan Garcia et al. |
| 2009/0022764 A1 | 1/2009 | Frater et al. |
| 2009/0028912 A1 | 1/2009 | Dave |
| 2009/0035237 A1 | 2/2009 | Maes et al. |
| 2009/0035238 A1 | 2/2009 | Pfluecker et al. |
| 2009/0035365 A1 | 2/2009 | Popplewell et al. |
| 2009/0053153 A1 | 2/2009 | Lee et al. |
| 2009/0053271 A1 | 2/2009 | Giner et al. |
| 2009/0130040 A1 | 5/2009 | Jonchiere |
| 2009/0196894 A1 | 8/2009 | Ehlis et al. |
| 2009/0232881 A1 | 9/2009 | Bandyopadhyay et al. |
| 2009/0252809 A1 | 10/2009 | Galeone et al. |
| 2009/0311336 A1 | 12/2009 | Jones et al. |
| 2009/0324652 A1 | 12/2009 | Polonka et al. |
| 2009/0324653 A1 | 12/2009 | Polonka et al. |
| 2009/0324654 A1 | 12/2009 | Polonka et al. |
| 2009/0324655 A1 | 12/2009 | Polonka et al. |
| 2010/0003204 A1 | 1/2010 | Loy et al. |
| 2010/0040696 A1 | 2/2010 | Sente et al. |
| 2010/0092408 A1 | 4/2010 | Breyfogle et al. |
| 2010/0111884 A1 | 5/2010 | Acker et al. |
| 2010/0112100 A1 | 5/2010 | Willemin et al. |
| 2010/0139704 A1 | 6/2010 | Bernard et al. |
| 2010/0158824 A1 | 6/2010 | Lin |
| 2010/0172849 A1 | 7/2010 | Shaow et al. |
| 2010/0183525 A1 | 7/2010 | Lin |
| 2010/0183529 A1 | 7/2010 | Richard et al. |
| 2010/0209463 A1 | 8/2010 | Pfluecker et al. |
| 2010/0284950 A1 | 11/2010 | Muller et al. |
| 2010/0322880 A1 | 12/2010 | Rudolph et al. |
| 2010/0322983 A1 | 12/2010 | Griffiths-Brophy et al. |
| 2010/0330018 A1 | 12/2010 | Lorant et al. |
| 2011/0034408 A1 | 2/2011 | Lorant |
| 2013/0011347 A1 | 1/2013 | Tanner et al. |
| 2013/0039963 A1 | 2/2013 | Lorant et al. |
| 2013/0224133 A1 | 8/2013 | Romanhole et al. |
| 2013/0230474 A1 | 9/2013 | Tanner |
| 2013/0243717 A1 | 9/2013 | Catalan et al. |
| 2013/0243834 A1 | 9/2013 | Tanner |
| 2013/0243835 A1 | 9/2013 | Tanner et al. |
| 2013/0243836 A1* | 9/2013 | Tanner ............... A61Q 19/00 424/401 |
| 2013/0336902 A1 | 12/2013 | Fernandez Prieto et al. |
| 2014/0288191 A1 | 9/2014 | Kim et al. |
| 2014/0302159 A1 | 10/2014 | Fageon et al. |
| 2015/0023895 A1 | 1/2015 | Finley et al. |
| 2015/0050321 A1 | 2/2015 | Gately et al. |
| 2015/0224046 A1 | 8/2015 | Lorant et al. |
| 2016/0367091 A9 | 12/2016 | Fernandez Prieto et al. |
| 2018/0008525 A1 | 1/2018 | Tanner et al. |

FOREIGN PATENT DOCUMENTS

| | | |
|---|---|---|
| DE | 10019314 C1 | 9/2001 |
| DE | 102009029218 A1 | 3/2011 |
| EP | 0281315 A2 | 9/1988 |
| EP | 0281395 A2 | 9/1988 |
| EP | 0319638 A1 | 6/1989 |
| EP | 0969807 A2 | 1/2000 |
| EP | 1077060 A1 | 2/2001 |
| EP | 1101527 A1 | 5/2001 |
| EP | 1138311 A1 | 10/2001 |
| EP | 1243318 A1 | 9/2002 |
| EP | 1243319 A1 | 9/2002 |
| EP | 1243320 A1 | 9/2002 |
| EP | 1243321 A1 | 9/2002 |
| EP | 1243322 A1 | 9/2002 |
| EP | 1243324 A1 | 9/2002 |
| EP | 1247568 A1 | 10/2002 |
| EP | 1302124 A2 | 4/2003 |
| EP | 1398073 A1 | 3/2004 |
| EP | 1398075 A1 | 3/2004 |

(56) References Cited

FOREIGN PATENT DOCUMENTS

| | | |
|---|---|---|
| EP | 1452163 A1 | 9/2004 |
| EP | 1462157 A1 | 9/2004 |
| EP | 1702674 A1 | 9/2006 |
| EP | 1797946 A2 | 6/2007 |
| EP | 1870077 A2 | 12/2007 |
| EP | 2174691 A1 | 4/2010 |
| EP | 2177201 A1 | 4/2010 |
| EP | 2382961 A2 | 11/2011 |
| EP | 1902704 B1 | 11/2013 |
| FR | 2800991 A1 | 5/2001 |
| FR | 2930429 A1 | 10/2009 |
| FR | 2938767 A1 | 5/2010 |
| FR | 2975287 A1 | 11/2012 |
| FR | 2975294 A1 | 11/2012 |
| FR | 2989884 A1 | 11/2013 |
| FR | 2999909 A1 | 6/2014 |
| FR | 3007646 A1 | 1/2015 |
| FR | 3008312 A1 | 1/2015 |
| GB | 2079179 A | 1/1982 |
| GB | 2422605 A | 8/2006 |
| JP | S61-102475 A | 5/1986 |
| JP | 63-208508 A | 8/1988 |
| JP | H022867 A | 1/1990 |
| JP | H03267140 A | 11/1991 |
| JP | H04305513 A | 10/1992 |
| JP | H06157253 A | 6/1994 |
| JP | 2002255741 A | 9/2002 |
| JP | 2005035910 A | 2/2005 |
| JP | 2005306942 A | 11/2005 |
| JP | 2006104141 A | 4/2006 |
| JP | 2008214279 A | 9/2008 |
| JP | 2009023955 A | 2/2009 |
| JP | 2009062327 A | 3/2009 |
| JP | 2009167168 A | 7/2009 |
| JP | 2010047525 | 3/2010 |
| JP | 2010064986 A | 3/2010 |
| JP | 2011219383 A | 11/2011 |
| JP | 2011256154 A | 12/2011 |
| JP | 2014101343 A | 6/2014 |
| JP | 2014101344 A | 6/2014 |
| KR | 20070052486 A | 5/2007 |
| KR | 20080020857 A | 3/2008 |
| KR | 20080026956 A | 3/2008 |
| KR | 20090069370 A | 7/2009 |
| KR | 20090075299 A | 7/2009 |
| KR | 20140055343 A | 5/2014 |
| WO | WO9607395 A1 | 3/1996 |
| WO | WO9614054 A1 | 5/1996 |
| WO | WO9629302 A1 | 9/1996 |
| WO | WO9707779 A1 | 3/1997 |
| WO | WO9963965 A1 | 12/1999 |
| WO | WO0040212 A1 | 7/2000 |
| WO | WO0100161 A1 | 1/2001 |
| WO | WO200166078 A1 | 9/2001 |
| WO | WO0203929 A1 | 1/2002 |
| WO | WO02076423 A2 | 10/2002 |
| WO | WO02078665 A1 | 10/2002 |
| WO | WO03011238 A2 | 2/2003 |
| WO | WO03030854 A1 | 4/2003 |
| WO | WO2004000918 A1 | 12/2003 |
| WO | WO2005025522 A2 | 3/2005 |
| WO | WO2005039512 A1 | 5/2005 |
| WO | WO2005102248 A2 | 11/2005 |
| WO | WO2005102255 A2 | 11/2005 |
| WO | WO2005102264 A1 | 11/2005 |
| WO | WO2006024768 A2 | 3/2006 |
| WO | WO2007000316 A1 | 1/2007 |
| WO | WO2007053424 A2 | 5/2007 |
| WO | WO2007075747 A2 | 7/2007 |
| WO | WO2007100416 A1 | 9/2007 |
| WO | WO2007109282 A2 | 9/2007 |
| WO | WO2008001269 A2 | 1/2008 |
| WO | WO2008002637 A2 | 1/2008 |
| WO | WO2008032342 A1 | 3/2008 |
| WO | WO2008040303 A1 | 4/2008 |
| WO | WO2008095144 A2 | 8/2008 |
| WO | WO2008126971 A1 | 10/2008 |
| WO | WO2008150947 A2 | 12/2008 |
| WO | WO2009006091 A2 | 1/2009 |
| WO | WO2009042509 A2 | 4/2009 |
| WO | WO2009042535 A2 | 4/2009 |
| WO | WO2009042732 A1 | 4/2009 |
| WO | WO2009042832 A2 | 4/2009 |
| WO | WO2012160289 A2 | 11/2012 |
| WO | WO2013076238 A1 | 5/2013 |
| WO | WO2013087926 | 6/2013 |
| WO | WO2014083116 A2 | 6/2014 |
| WO | WO2014096320 A2 | 6/2014 |
| WO | WO2014128678 A1 | 8/2014 |
| WO | WO2014128679 A1 | 8/2014 |

OTHER PUBLICATIONS

International Search Report and Written Opinion of the International Searching Authority, PCT/US2012/042221, dated May 9, 2014, 8 pages.

International Search Report and Written Opinion of the International Searching Authority, PCT/US2012/042228, dated Apr. 22, 2014, 9 pages.

International Search Report and Written Opinion of the International Searching Authority, PCT/US2012/045646, dated Mar. 4, 2014, 11 pages.

International Search Report and Written Opinion of the International Searching Authority, PCT/US2012/045687, dated Feb. 26, 2014, 11 pages.

International Search Report and Written Opinion of the International Searching Authority, PCT/US2013/028578, dated Feb. 20, 2014, 9 pages.

International Search Report and Written Opinion of the International Searching Authority, PCT/US2013/032921, dated Oct. 9, 2014, 10 pages.

International Search Report and Written Opinion of the International Searching Authority, PCT/US2013/032922, dated Aug. 8, 2014, 13 pages.

International Search Report and Written Opinion of the International Searching Authority, PCT/US2016/039934, dated Sep. 9, 2016, 14 pages.

Yamaguchi, Rapid Swelling and Pattern Formation in Hydrogel Particles, Journal of the Society of Rheology, Japan, 2014, vol. 42, No. 2, pp. 129-133.

Zhang et al., Study on Structure and Molecular Dynamics of Starch/Poly (sodium acrylate)-grafted Superabsorbent by C Solid State NMR, Fibers and Polymers 2008, vol. 9, No. 3, 271-275.

* cited by examiner

SUPERABSORBENT POLYMERS AND STARCH POWDERS FOR USE IN SKIN CARE COMPOSITIONS

FIELD OF THE INVENTION

The present invention relates to the combination of superabsorbent polymers and high levels of waxes and powder particulates, e.g. starch powders, for use in improving the look, feel and stability of skin care products.

BACKGROUND OF THE INVENTION

Personal care products are well known and widely used. These products have long been employed to protect, cleanse and moisturize, deliver actives, hide imperfections and reduce the oiliness and shine on keratinous surfaces. A variety of personal-care compositions are available to provide skin care benefits and to help prevent and even counteract what many consumers consider to be undesirable signs of skin aging such as fine lines, wrinkles, and uneven skin texture. The look and feel of the compositions are also important to consumers.

In order to achieve compositions with new and desirable look and feel aesthetics, one approach has been altering the physical properties of natural oils or fats to achieve butters that are spreadable on skin. Butters possess attributes that are different from traditional solids and liquids in that they are solid when applied but may liquefy under pressure. Body butter products typically consist of oil-in-water emulsions that contain butters and other waxy materials. The waxy materials give these products a more solid-like consistency than most traditional skin care moisturizer products. Importantly, the formulations appear to melt into the skin as they are applied. Thus consumers like these butter products since they look rich and creamy. However, after they are applied to the skin these butter products, having waxy materials, may look shiny or may feel sticky, greasy, or heavy.

In addition, most butter product formulations in the literature and market utilize conventional aqueous thickeners, such as carbomers and similar polymers. Thus, for example, in the case of carbomers, the so-called "quick-breaking effect" may be observed. The "quick-breaking effect" is understood as the phenomenon where, in the case of contact of the emulsion with the electrolytes of the skin, the emulsion immediately breaks. This phenomenon is evident from an "aqueous sliding away" upon rubbing in and is often perceived as unpleasant by consumers.

Thus, surprisingly it has been found that the inclusion of high levels of powder particulates, such as spherical starch powders, and higher levels of waxy materials with optimal wax/oil ratios, yields significant improvement in the in-use aesthetics of these compositions. These compositions thus maintain a rich, luxurious, thick and creamy appearance prior to use, as well as deliver a superior in use experience. These improved compositions feel less sticky, greasy, or heavy after they are applied to the skin. If the level of powder is too high, the product may be harder to spread on skin and such products can also become noticeably white and can flake off the skin.

In addition to further enhance the improved skin feel upon application to skin, the present compositions comprise alternative superabsorbent polymers thickeners. These superabsorbent polymer thickeners further enhance the skin feel during application. Specifically these products provide better spreading during application, less stickiness, and a less oily or greasy look and feel.

Accordingly, there is a need to provide skin care moisturizing formulations that comprise higher levels of oil components, wax materials, and powder particulates, along with superabsorbent polymer thickeners, at optimized ratios. This system not only looks rich, luxurious, thick and creamy, additionally it delivers rub-in characteristics of conventional butter products, but with a lighter, less-sticky, less-greasy, and a superior smooth feel which is both new and unexpected.

SUMMARY OF THE INVENTION

The present invention relates to a skin care composition comprising:
an oil phase mixture comprising from about 5% to about 30% by weight of the composition, of a wax material; and optionally from about 1% to about 20% by weight of the composition, of an oil that is liquid at room temperature; the oil phase mixture having a melting point of about 25° C. to about 50° C.;
a water phase comprising from about 0.1% to about 5%, by weight of the composition, of a superabsorbent polymer; and from about 20% to about 85% by weight of the composition of water; and
from about 6% to about 30%, by weight of the composition, of particulate material selected from the group consisting of starch particles, silicone elastomer particles and combinations thereof; wherein the composition is an oil in water emulsion.

The present invention further relates to a skin care composition comprising:
an oil phase mixture comprising from about 5% to about 30% by weight of the composition, of a wax material; and from about 1% to about 20% by weight of the composition, of an oil that is liquid at room temperature; the oil phase mixture having a melting point of about 25° C. to about 50° C.; a water phase comprising from about 0.1% to about 5%, by weight of the composition, of a superabsorbent polymer; and from about 20% to about 80% by weight of the composition, of water; and
from about 8% to about 25%, by weight of the composition, of non-crosslinked starch particles; wherein the composition is an oil in water emulsion; the composition has a viscosity at 25° C. of about 100,000 cP to about 2,000,000 cP; and wherein the ratio of wax material to oil is from about 2:1 to about 20:1.

DETAILED DESCRIPTION OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the epidermis.

"Keratinous tissue" refers to keratin-containing layers disposed as the outermost protective covering of mammals (e.g., humans, dogs, cats, etc.) which includes, but is not limited to, skin, lips, hair, toenails, fingernails, cuticles, hooves, etc.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Non-UV" means a material not recognized by a skilled artisan in the field of sunscreen formulation to be a dermatologically acceptable UV active absorbing material.

"UV active" means a material recognized by a skilled artisan in the field of sunscreen formulation to be a dermatologically acceptable UV active absorbing material. Such UV actives may be described as being UV-A and/or UV-B active agents. Approval by a regulatory agency is generally required for inclusion of active agents in formulations intended for human use. Those active agents which have been or are currently (per 21 C.F.R. part 352) approved by the U.S. Food and Drug Administration as acceptable for use in over-the counter sunscreen drug products include organic and inorganic substances including, without limitation, para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the U.S. but are approved for over the counter use in other regions or countries such as Europe (per European Commission's Cosmetic Directive Regulation), Japan, China, Australia, New Zealand, or Canada include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. However, as the list of approved materials is currently expanding, those of ordinary skill will recognize that the invention is not limited to UV actives currently approved for human use but are readily applicable to those that may be allowed in the future.

"Leave-on," in reference to compositions, means compositions intended to be applied to and allowed to remain on the keratinous tissue. These leave-on compositions are to be distinguished from compositions which are applied to the skin and subsequently (in a few minutes or less) removed either by washing, rinsing, wiping, or the like. Leave-on compositions exclude rinse-off applications such as shampoos, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying or other processing surfactants that are not intended to provide any significant cleansing benefits when applied topically to the skin.

"Derivatives" means an ester, ether, amide, hydroxy, and/or salt structural analogue of the relevant compound.

"Soluble" means at least about 0.1 g of solute dissolves in 100 ml of solvent, at 25° C. and 1 atm of pressure.

Oil Phase Mixture

The thickened aqueous phase of this invention may be combined with, or emulsified with an oil phase mixture to form an emulsion such as an oil-in-water emulsion.

In an embodiment the composition may comprise an oil phase mixture having from about 5% to about 30% by weight of the composition of a wax material, optionally an oil that is liquid at room temperature; the oil phase mixture having a melting point of about 25° C. to about 50° C., preferably from about 27° C. to about 45° C., or from about 28° C. to about 40° C.

Alternatively the oil phase mixture may comprise from about 5% to about 30% by weight of the composition of a wax material; from about 1% to about 20% of an oil that is liquid at room temperature, the oil phase mixture having a melting point of about 25° C. to about 50° C., preferably from about 27° C. to about 45° C., or from about 28° C. to about 40° C.

The total oil phase mixture comprises from about 6% to about 40%, by weight of the composition, more preferably from about 8% to about 30%, or about 10% to about 20%, by weight of the composition.

The higher levels of wax materials gives these compositions a thicker, more solid-like consistency than most traditional skin care moisturizer products. Importantly, in an embodiment the wax materials are combined with oily liquids so that the resulting oil phase mixture has a melting point so that the formulations appear to melt into the skin as they are applied.

Wax Materials

The wax material herein is a lipophilic ingredient that is solid or semi-solid at room temperature, and has a melting point of 25° C. to 80° C., preferably from 30° C. to 65° C. The level of wax is from 5% to 30%, preferably 6% to 25%, more preferably 8% to 22%, more preferably from 10% to 20% by weight of the composition.

Suitable wax materials include natural and synthetic materials, and include a variety of chemistries such as hydrocarbon waxes, ester waxes, alcohol waxes, silicone waxes, and mixtures thereof. Hydrocarbon waxes consist of only carbon and hydrogen atoms, and include for example polyethylene waxes, paraffin waxes, microcrystalline waxes, ceresin wax, ozokerite, and mixtures thereof. Another suitable example of hydrocarbon wax is Cirebelle 303, a synthetic hydrocarbon wax from Arch Personal Care Products.

Ester waxes are wax materials that contain at least one ester group. Suitable examples of naturally derived ester waxes include waxes obtained from the hydrogenation of oils from plant or animal sources, such as hydrogenated coconut oil, hydrogenated castor oil, hydrogenated olive oil, hydrogenated jojoba oil, and hydrogenated sunflower oil. Additional naturally derived ester waxes include beeswax, candelilla wax, carnauba wax, japan wax, montan wax, shea butter, cocoa butter, mango butter, and mixtures thereof.

Suitable examples of synthetic ester waxes include cetyl palmitate, cetyl stearate, pentaerythrityl distearate, and mixtures thereof.

Alcohol waxes are wax materials that contain at least one alcohol group. Suitable examples of alcohol waxes include myristyl alcohol, cetyl alcohol, stearyl alcohol, behenyl alcohol, and mixtures thereof.

Silicone waxes are wax materials that contain at least one silicon atom. Examples of suitable silicone waxes include the ABIL Wax series of alkyl silicones from Evonik, including for ABIL Wax 2434 (stearoxy dimethicone), ABIL Wax 2440 (behenoxy dimethicone), and ABIL Wax 9810P (C24-28 alkyl dimethicone). Additional examples of suitable silicone waxes include Dow Corning 2503 Wax (stearyl dimethicone and octadecene) from Dow Corning, Dow Corning SW-8005 C30 Resin Wax (C30-45 alkyldimethylsilyl polypropylsilsesquioxane) from Dow Corning, and Dow Corning 580 Wax (Stearoxy trimethylsilane and stearyl alcohol).

Preferred wax materials include silicone waxes, alcohol waxes, and ester waxes, and mixtures thereof. Especially preferred wax materials include the silicone waxes, alcohol waxes, and mixtures thereof.

Oils

The composition herein may comprise from about 1% to about 20%, preferably 1% to 15%, more preferably from 2% to 8% by weight of the composition, of an oil that is liquid at room temperature. Oils may be used to solubilize, disperse, or carry materials that are not suitable for water or water soluble solvents.

The oils may be volatile or nonvolatile. "Non-volatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C. Volatile oils may be used to provide a lighter feel when a heavy, greasy film is undesirable. Suitable oils include hydrocarbons, esters, amides, ethers, silicones, and mixtures thereof.

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, butyloctyl salicylate, phenylethyl benzoate, dicaprylyl carbonate, dioctyl malate, dicaprylyl maleate, isononyl isononanoate, propylene glycol dicaprate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters". Other esters suitable for use in the personal care composition include those known as polyhydric alcohol esters and glycerides.

Other suitable oils include amides. Amides include compounds having an amide functional group while being liquid at 25° C. and insoluble in water. Suitable amides include, but are not limited to, N-acetyl-N-butylaminopropionate, isopropyl N-lauroylsarcosinate, butylphthalimide, isopropylphthalimide, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include, but are not limited to, $C_{4-20}$ alkyl ethers of polypropylene glycols, and di-$C_{8-30}$ alkyl ethers. Suitable examples of these materials include PPG-14 butyl ether, PPG-15 stearyl ether, PPG-11 stearyl ether, dioctyl ether, dodecyl octyl ether, and mixtures thereof.

Suitable silicone oils include polysiloxanes. Polysiloxanes may have a viscosity of from about 0.5 to about 1,000,000 centistokes at 25° C. Such polysiloxanes can be represented by the general chemical formula:

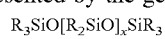

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular weight. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable dimethicones include those represented by the chemical formula:

wherein R and R' are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as s 2502 Cosmetic Fluid from Dow Corning or as Abil Wax 9801 or 9814 from Evonik Goldschmidt GmbH.

Cyclic silicones are one type of silicone oil that may be used in the composition. Such silicones have the general formula:

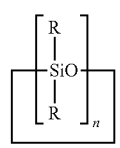

wherein R is independently selected from hydrogen or $C_{1-30}$ straight or branched chain, saturated or unsaturated alkyl, phenyl or aryl, trialkylsiloxy; and where n=3 to 8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Ratios of Wax Material and Oil

In an embodiment the ratio of wax material to oil is from about 2:1 to about 20:1, preferably from about 3:1 to about 10:1.

Water Phase

The skin care composition further comprises a water phase comprising: from about 0.1% to about 5%, by weight, of a superabsorbent polymer, preferably from about 0.2% to about 3% or from about 0.4% to about 1.5% by weight of the composition, and from about 20% to about 85%, by weight of the composition, of water wherein the composition is an emulsion such as an oil in water emulsion.

Superabsorbent Polymer

The superabsorbent polymer can be present in the composition of the invention ranging, for example, from 0.1% to 5% by weight, preferably from 0.2% to 3% by weight, preferably from 0.4% to 1.5% by weight with respect to the total weight of the composition.

These polymers have a high capacity for absorbing and retaining water and aqueous fluids. After absorption of the aqueous liquid, the particles of the polymer thus impregnated with aqueous fluid remain insoluble in the aqueous fluid and thus retain their separated particulate state.

In an embodiment the term "superabsorbent polymer" is understood to mean a polymer which is capable, in its dry state, of spontaneously absorbing at least 20 times its own weight of aqueous fluid, in particular of water and especially of distilled water. Such superabsorbent polymers are described in the work "Absorbent Polymer Technology, Studies in Polymer Science 8" by L. Brannon-Pappas and R. Harland, published by Elsevier, 1990.

The superabsorbent polymer can have a water-absorbing capacity ranging from 20 to 2000 times its own weight (i.e., 20 g to 2000 g of water absorbed per gram of superabsorbent polymer), preferably from 30 to 1500 times and alternatively ranging from 50 to 1000 times. These water-absorbing characteristics are defined at standard temperature (25° C.) and pressure (760 mm Hg, i.e. 100 000 Pa) conditions and for distilled water. The value of the water-absorbing capacity of a polymer can be determined for example by dispersing 0.5 g of polymer(s) in 150 g of a water solution, by waiting 20 minutes, by filtering the nonabsorbed solution through a 150 µm filter for 20 minutes and by weighing the nonabsorbed water.

Superabsorbent polymers are commonly made from the polymerization of acrylic acid blended with sodium hydroxide in the presence of an initiator to form a poly-acrylic acid sodium salt (sometimes referred to as sodium polyacrylate). This polymer is the most common type of superabsorbent polymers made in the world today. Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile to name a few. The latter is one of the oldest superabsorbent polymers forms created. Today superabsorbent polymers are made using one of three primary methods; gel polymerization, suspension polymerization or solution polymerization.

Gel Polymerization involves a mixture of frozen acrylic acid, water, cross-linking agents and UV initiator chemicals are blended and placed either on a moving belt or in large tubs. The liquid mixture then goes into a "reactor" which is a long chamber with a series of strong UV lights. The UV radiation drives the polymerization and cross-linking reactions. The resulting "logs" are sticky gels containing 60-70% water. The logs are shredded or ground and placed in various sorts of driers. Additional cross-linking agent may be sprayed on the particles' surface; this "surface cross-linking" increases the product's ability to swell under pressure—a property measured as Absorbency Under Load (AUL) or Absorbency Against Pressure (AAP). The dried polymer particles are then screened for proper particle size distribution and packaging. The Gel Polymerization (GP) method is currently the most popular method for making the sodium polyacrylate superabsorbent polymers now used in baby diapers and other disposable hygienic articles.

Solution polymers, those made by solution polymerization, offer the absorbency of a granular polymer supplied in solution form. Solutions can be diluted with water prior to application. Solutions can coat most substrates or be used to saturate the substrates. After drying at a specific temperature for a specific time, the result is a coated substrate with superabsorbent functionality. For example, this chemistry can be applied directly onto wires & cables, though it is especially optimized for use on components such as rolled goods or sheeted substrates.

Solution based polymerization is commonly used today for SAP (superabsorbent polymer) manufacture of co-polymers, particularly those with the toxic acrylamide monomer. This process is efficient and generally has a lower capital cost base. The solution process uses a water based monomer solution to produce a mass of reactant polymerized gel. The polymerization's own reaction energy (exothermic) is used to drive much of the process, helping reduce manufacturing cost. The reactant polymer gel is then chopped, dried and ground to its final granule size. Any treatments to enhance performance characteristics of the SAP are usually accomplished after the final granule size is created.

Superabsorbent polymers can also be made by suspension polymerization. This process suspends the water-based reactant in a hydrocarbon-based solvent. The net result is that the suspension polymerization creates the primary polymer particle in the reactor rather than mechanically in post-reaction stages. Performance enhancements can also be made during, or just after, the reaction stage.

The superabsorbent polymer used in the composition of the invention is preferably provided in the form of particles which, once hydrated, swell with the formation of soft particles having a weight-average diameter of 10 µm to 300 µm, in another embodiment from 20 µm to 200 µm and in another embodiment from about 40 µm to 150 µm. These particles sizes relate to the primary particles.

In one embodiment the superabsorbent polymer, in its non-swollen (dry) state, exhibits a weight-average particle size of from 2 µm to 100 µm, preferably from 4 µm to 50 µm, or from 5 µm to 30 µm, and/or from 10 µm to 20 µm. These particles sizes relate to the primary particles. The superabsorbent polymer can, for instance, be spherical shaped, such as substantially spherical or true spheres or irregularly shaped. Preferably the superabsorbent polymer is irregularly shaped (e.g. such as may be produced by a grinding or milling process).

The superabsorbent polymers used in the present invention are preferably crosslinked acrylic homo- or copolymers and derivatives which are preferably neutralized and which are provided in the particulate form.

Mention may in particular be made of the polymers chosen from: crosslinked sodium polyacrylates, such as, for example, those sold under the names Octacare X100, X110 and RM100 by Avecia, those sold under the names Flocare GB300 and Flosorb 500 by SNF, those sold under the names Luquasorb 1003, Luquasorb 1010, Luquasorb 1280 and Luquasorb 1100 by BASF, those sold under the names Water Lock G400 and G430 (INCI name: Acrylamide/Sodium Acrylate Copolymer) by Grain Processing, or Aqua Keep 10 SH NF, Aqua Keep 10 SH NFC, sodium acrylate crosspolymer-2, provided by Sumitomo Seika, starches grafted by an acrylic polymer (homopolymer or copolymer) and in particular by sodium polyacrylate, such as those sold under the names Sanfresh ST-100C, ST100MC and IM-300MC by Sanyo Chemical Industries (INCI name: Sodium Polyacrylate Starch), hydrolysed starches grafted by an acrylic polymer (homopolymer or copolymer), in particular the acryloacrylamide/sodium acrylate copolymer, such as those sold under the names Water Lock A-240, A-180, B-204, D-223, A-100, C-200 and D-223 by Grain Processing (INCI name: Starch/Acrylamide/Sodium Acrylate Copolymer).

In an embodiment superabsorbent polymers include starch grafted polymer or copolymers such as sodium polyacrylate starch; sodium carboxymethyl starch; hydrolysed starches grafted by an acrylic polymer or copolymer such as acryloacrylamide/sodium acrylate copolymer; starch/acrylates/acrylamide copolymer; and combinations thereof.

In one embodiment the superabsorbent polymer is sodium polyacrylate starch. Preferred superabsorbent polymers include Makimousse 12 and Makimouse 25 supplied by Kobo Products Inc.

Particulate Material

The skin care composition also comprises from about 6% to about 30%, by weight, alternatively from about 8% to about 25%, and alternatively from about 10% to about 16%, by weight of the composition of particulate material selected from the group consisting of starch particles, silicone elastomer particles and combinations thereof. These particulates can, for instance, be spherical (e.g. substantially spherical), or irregularly shaped; surface coated or uncoated; porous or non-porous; charged or uncharged; and can be added to the current compositions as a powder or as a pre-dispersion.

The particulate material provides a light diffusing effect that provides a smooth look to the skin that is often more natural looking than makeup. Alternatively or additionally, the particulate material may provide a silky or lubricious feel that can offset the undesirable greasiness associated with oils and/or the undesirable tacky feel associated with some humectants. It is important for the composition to include suitable levels of particles. If too much particulate material is present, then the look and feel benefits provided herein may level off or even start to decline. In particular, the powder particulates may no longer remain evenly distributed on the skin surface, which can lead to undesirable whitening (e.g., because particulate no longer remain wetted) and/or flaking from the skin (e.g., because the particulates no longer suitably adhere to the rest of the product film). On the other hand, if too little is present in the composition, then the undesirable look and/or feel properties of the skin care composition may not be altered as desired.

It is believed, without being limited by theory, that the size of the particles is also important for delivering visible texture benefits on skin. In particular, it is important that the particles are large enough to protrude from the dry film formed by the skin care product on the skin (i.e., at least a portion of each (or most) of the particle(s) extends out of the surface of the film). In this way, a "rough" film is created, which diffusely reflects light (i.e., creates a bumpy-looking surface) and reduces the surface area of the underlying skin care product film that can be contacted by a user's hand or other object (i.e., reduces the tacky and/or greasy feel of the skin care composition, etc.). But as particle size increases, the number of particles in the composition decreases. For substantially spherical particles, the number of particles per unit volume is proportional to the inverse of the cube of the particle diameter. Thus, using relatively large particles at a fixed amount (i.e., weight percent) in the product effectively reduces the number of particles that can be added. On the other hand, using smaller particles may increase the number of particles present in the composition, but may not provide the desired "rough surface" to the product film because a smaller portion of each particle (or even no portion of the particle) extends above the surface of the product film.

On average, the dry film thickness of a conventional skin care product, when used as intended, typically ranges between 1 and 6 microns. Consequently, it is important to ensure that the selected particle size is appropriate for the skin care product. Particle sizes herein can be determined by any suitable method known in the art, such as by using coulter-counter equipment or the ASTM Designation E20-85, titled "Standard Practice for Particle Size Analysis of Particulate Substances in the Range of 0.2 to 75 Micrometers by Optical Microscopy," ASTM Volume 14.02, 1993. These particle sizes are weight average particle sizes.

These particles may substantially spherical (i.e., the majority or even all the particles in the composition are spherical). It is believed, without being limited by theory, that spherical particles generally provide a more suitable product feel relative to non-spherical particles, at least in part because a spherical particle creates less drag and rolls more smoothly across a surface than a non-spherical particle. As used herein, "spherical" and "sphere" mean particles that have an aspect ratio (i.e., ratio of major axis to minor axis) of from 1:1 to 2:1, (e.g., 1:1 to 2:1, 1:1 to 1.6:1 or even 1:1 to 1.4:1). The shape of the particles may be determined by any suitable method known in the art (e.g., optical microscope or electron microscope and suitable image analysis software).

In some instances, the composition comprises silicone elastomer particles that are preferably spherical (e.g. substantially spherical) silicone elastomer particles. For example, the composition may include from 6% to 30% by weight of the composition of spherical silicone elastomer particles (e.g., from 8% to 25% or even 10% to 16%). The amount of silicone elastomer powder particle is determined based on the particulate material being in neat form (i.e., not swollen in solvent). It may be desirable to provide spherical silicone elastomer particles that have no tackiness and a rubber hardness (as measured by Durometer A defined in JIS K 6253) in the range of 10 to 90, (e.g., 20 to 80 or even from 25 to 75). When the rubber hardness is less than 5, the resulting silicone particles tend to become agglomerated, and dispersion into primary particles can be difficult. In contrast, a rubber hardness in excess of 90 may invite loss of soft texture that undesirably affects the feel properties provided by the finisher.

The spherical silicone elastomer particles herein may have a weight average particle size of from 1 μm to 40 μm, (e.g., from 2 μm to 30 μm or even from 5 μm to 15 μm). Of course, it is to be appreciated that the particle sizes disclosed herein may be readily adapted for use with thicker or thinner films without departing from the spirit and scope of the present invention.

Silicone elastomer particles suitable for use herein may be prepared from a variety of silicone materials, e.g., organopolysiloxanes such as cured silicone rubbers and poly(organosilsesquioxane) resins. The silicone elastomer particles suitable herein may be coated or uncoated. For example, the silicone particles may include silicone resin-coated silicone rubber particles (e.g., silicone rubber particles with polyorganosilsesquioxane attached to their surface). Commercially available silicone particles suitable for use in the present invention include: KSP-100, -101, -102, -103, -104, and -105, all from Shin Etsu; and DC9506 and DC 9701 from Dow Corning. One non-limiting example of useful silicone elastomers is crosslinked organopolysiloxane (or siloxane) elastomers, as described in U.S. patent publication 2003/0049212A1.

Silicone elastomer particles suitable for the present invention may be surface treated or coated, and silicone resin-coated silicone rubber particles are preferred.

In some instances, the present composition may include from 6% to 30%, by weight of the composition, or 8% to 25% by weight, of starch particles, preferably spherical starch particles (or preferably from 10% to 16%). The starch particles suitable for use herein may be coated or uncoated (e.g., coated with a suitable silicone material). In some instances, the starch particles may be a coated or uncoated starch derivative. In one embodiment, the particulate starch material is hydrophobically coated. The starch particles herein may have a weight average particle size of from 1 μm to 40 μm, (e.g., from 2 μm to 30 μm or even from 5 μm to 30 μm or from 5 μm to 25 μm). Particle size can be determined by any suitable method known in the art, such as by using coulter-counter equipment or the ASTM Designation E20-85, titled "Standard Practice for Particle Size Analysis of Particulate Substances in the Range of 0.2 to 75 Micrometers by Optical Microscopy," ASTM Volume 14.02, 1993.

Some non-limiting examples of commercially available starch particles suitable for use herein are tapioca starch (available as Tapioca Pure from AkzoNobel), corn starch (available as Purity 21C from AkzoNobel), potato starch, glyceryl starch (available as Dry-Flo GS from AkzoNobel), aluminum starch octenylsuccinate (available as Mackaderm ASTO-Dry from Rhodia, Inc., and Dry-Flo PC from AkzoNobel), calcium starch octenylsuccinate (available as Skin Flow C from MGP Ingredients, Inc., and Mackaderm CSTO-Dry from Rhodia, Inc.), and polymethylsilsesquioxane coated tapioca starch (available as Dry-Flo TS from AkzoNobel).

In one embodiment the starch particles suitable for use herein are selected from the group consisting of coated starch, uncoated starch, non crosslinked starch such as tapioca starch (available as Tapioca Pure from AkzoNobel) and polymethylsilsesquioxane coated tapioca starch (available as Dry-Flo TS from AkzoNobel). In one embodiment the starch particles are non-crosslinked starch particles.

Viscosity

In one embodiment the composition of the present invention is a composition or an emulsion having viscosity at 25° C. of about 100,000 cP to about 2,000,000 cP, more preferably from about 200,000 cP to about 1,000,000 cP. Viscosity is determined by a Brookfield RVT, at 5 RPM using Spindle T-E.

Additional Thickening Agents

The composition of the present invention may include one or more additional thickening agents. The composition of the present invention may comprise from about 0.1% to about 5%, or, alternatively, from about 0.2% to about 2%, of a thickening agent when present. Suitable classes of thickening agents include but are not limited to carboxylic acid polymers, polyacrylamide polymers, sulfonated polymers, copolymers thereof, hydrophobically modified derivatives thereof, gums, celluloses, and mixtures thereof.

Suitable thickening agents include carboxylic acid polymers such as the carbomers (e.g., the CARBOPOL® 900 series such as CARBOPOL® 954). Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as CARBOPOL® 1342, CARBOPOL® 1382, PEMULEN TR-1, and PEMULEN TR-2, from Noveon, Inc.

Other suitable thickening agents include the polyacrylamide polymers and copolymers. An exemplary polyacrylamide polymer has the CTFA designation "polyacrylamide and isoparaffin and laureth-7" and is available under the trade name SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500 W, SSSA100H, from Lipo Chemicals, Inc., (Patterson, N.J.).

Other suitable thickening agents useful herein are sulfonated polymers such as the CTFA designated sodium polyacryloyldimethyl taurate available under the trade name Simulgel 800 from Seppic Corp. and Viscolam At 100 P available from Lamberti S.p.A. (Gallarate, Italy). Another commercially available material comprising a sulfonated polymer is Sepiplus 400 available from Seppic Corp.

"Gum" is a broadly defined term in the art. Gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, derivatives thereof and mixtures thereof.

Natural gums are polysaccharides of natural origin, capable of causing a large viscosity increase in solution, even at small concentrations. They can be used as thickening agents, gelling agents, emulsifying agents, and stabilizers. Most often these gums are found in the woody elements of plants or in seed coatings. Natural gums can be classified according to their origin. They can also be classified as uncharged or ionic polymers (polyelectrolytes), examples of which include the following. Natural gums obtained from seaweeds, such as: agar; alginic acid; sodium alginate; and carrageenan. Natural gums obtained from non-marine botanical resources include: gum arabic, from the sap of Acacia trees; gum ghatti, from the sap of *Anogeissus* trees; gum tragacanth, from the sap of *Astragalus* shrubs; karaya gum, from the sap of *Sterculia* trees. Examples of uncharged gums include: guar gum, from guar beans, locust bean gum, from the seeds of the carob tree; beta-glucan, from oat or barley bran; chicle gum, an older base for chewing gum obtained from the chicle tree; dammar gum, from the sap of Dipterocarpaceae trees; glucomannan from the konjac plant; mastic gum, a chewing gum from ancient Greece obtained from the mastic tree; psyllium seed husks, from the *Plantago* plant; spruce gum, a chewing gum of American Indians obtained from spruce trees; tara gum, from the seeds of the tara tree. Natural gums produced by bacterial fermentation include gellan gum and xanthan gum.

Suitable thickening agents include cellulose and modified cellulosic compositions such as, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers some portion of the hydroxy groups of the cellulose polymer are hydroyxalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Emulsifiers

The compositions of this invention may comprise an emulsifier. An emulsifier is particularly suitable when the phase is in the form of an emulsion or if immiscible materials are being combined. The composition may comprise from about 0.01%, 0.05%, or 0.1% to about 10%, 5%, or 2% emulsifier, and/or from about 0.01% to about 5%, and/or from about 0.05% to about 2%, and/or from about 0.1% to about 0.5%, emulsifier. Emulsifiers may be nonionic, anionic or cationic, preferably nonionic. Non-limiting examples of emulsifiers are disclosed in U.S. Pat. Nos. 3,755,560, 4,421,769, and McCutcheon's, *Emulsifiers and Detergents,* 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof. In one embodiment the emulsifier is selected from a group consisting of ethers of glycerol, polyglycerol, sucrose, glucose, or sorbitol; esters of glycerol, polyglycerol, sucrose, glucose, or sorbitol; and mixtures thereof.

Silicone emulsifiers may be used. Linear or branched type silicone emulsifiers may also be used. Particularly useful silicone emulsifiers include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin Etsu.

Skin Care Active

The compositions of the present invention may comprise at least one additional skin care active. Many skin care actives may provide more than one benefit, or operate via more than one mode of action; therefore, classifications herein are made for the sake of convenience and are not intended to limit the active to that particular application or applications listed.

UV Actives

The compositions of this invention may comprise a UV active. As used herein, "UV active" includes both sunscreen agents and physical sunblocks. Suitable UV actives may be organic or inorganic. Suitable UV actives are listed in the functional category of "Sunscreen Agents" in the Personal Care Product Council's *International Cosmetic Ingredient Dictionary and Handbook*, Thirteenth Edition, 2010. The composition may comprise from may comprise an amount of UV active prescribed or proposed by regulatory agencies in the US (e.g., 21 CFR part 352, 68 Federal Register 41386, 70 Federal Register 72449, or 71 Federal Register 42405), Europe (Regulation No 1223/2009 of the EU Parliament; Annex VI), Japan, China, Australia, New Zealand, or Canada. In particular embodiments, the composition comprises from about 1%, 2%, or 3% to about 40%, 30%, or 20%, by weight of the composition, UV active. In another embodiment, the composition may comprise a sufficient about of UV active to yield a Sun Protection Factor of at least about 15, 30 45, or 50. SPF testing is conventional and well understood in the art. A suitable SPF test is prescribed in 21 C.F.R. 352, Subpart D.

Suitable UV actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxy dibenzoylmethane, 4-tert-butyl-4'-methoxy dibenzoylmethane (i.e., butyl methoxydibenzoylmethane or avobenzone) (commercially available as PARSOL® 1789 from DSM), 2-methyl-5-isopropyl-4'-methoxy dibenzoylmethane, 2-methyl-5-tert-butyl-4'-methoxydibenzoylmethane, 2,4-dimethyl-4'-methoxy dibenzoylmethane, and 2,6-dimethyl-4-tert-butyl-4'-methoxy dibenzoylmethane. Other suitable UV actives include 2-ethylhexyl-p-methoxycinnamate (commercially available as PARSOL® MCX from DSM), 2-hydroxy-4-methoxybenzophenone, benzonphenone-3 (i.e. oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl salicylate, homomenthyl salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5- sulfonicbenzoxazoic acid, octocrylene, zinc oxide, titanium dioxide, and mixtures of these compounds.

Other suitable UV actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), ethylhexyl triazone (commercially available as Uvinul® T 150 from BASF), drometrizole trisiloxane (marketed as Mexoryl XL by L'Oreal), sodium dihydroxy dimethoxy disulfobenzophenone (i.e., benzophenone-9, commercially available as Uvinul® DS 49 from BASF), diethylamino hydroxybenzoyl hexyl benzoate (commercially available as Uvinul® A Plus from BASF), diethylhexyl butamido triazone (i.e., Iscotrizinol, commercially available as Uvasorb® HEB by 3V Sigma), polysilicone-15 (i.e., commercially available as PARSOL® SLX from DSM), isoamyl p-methoxycinnamate (i.e., amiloxate, commercially available as Neo Heliopan® E 1000 from Symrise), and mixtures thereof.

The UV actives of the present invention may be encapsulated. Examples of commercially available encapsulated sunscreen actives include, but are not limited to: Eusolex UV-Pearls 2292 (Merck/EMD Chemicals), which includes water, ethylhexyl methoxycinnamate, silica, phenoxyethanol, PVP, chlorphenesin, disodium EDTA, and BHT; Silasoma ME (Seiwa Kasei Co., Ltd), which includes water, polysilicone-14, and ethylhexyl methoxycinnamate; Silasoma MEA (Seiwa Kasei Co., Ltd), which includes water, polysilicone-14, ethylhexyl methoxycinnamate, and butyl methoxydibenzoylmethane; Silasoma MEP(S) (Seiwa Kasei Co., Ltd), which includes water, ethylhexyl methoxycinnamate, diethylamino hydroxybenzoyl hexyl benzoate, and polysilicone-14; Suncaps 664 (Particle Sciences, Inc.), which includes, ethylhexyl methoxycinnamate, synthetic beeswax, PEG-20, copernicia cerifera (carnauba) wax, Bis-PEG-12 dimethicone, beeswax, VP/Eicosene copolymer, sorbitan tristearate, steareth-100, and PEG-100 stearate; Suncaps 903 (Particle Sciences, Inc.), which includes ethylhexyl methoxycinnamate, benzophenone-3, synthetic beeswax, PEG-20, copernicia cerifera (carnauba) wax, Bis-PEG-12 dimethicone, beeswax, VP/Eicosene copolymer, sorbitan tristearate, steareth-100, and PEG-100 stearate; UV Pearls OMC (Sol Gel Technologies), which includes ethylhexyl methoxycinnamate, and silica; OMC-BMDBM (Sol Gel Technologies), which includes ethylhexyl methoxycinnamate, butyl methoxydibenzoylmethane, and silica; Tinosorb S Aqua (BASF), which includes, bis-ethylhexyloxyphenol methoxyphenyl triazine, and polymethyl methacrylate; Hybrid ABOS (Kobo), which includes, polymethylmethacrylate, butyl methoxydibenzoylmethane, and octyl salicylate; and Hybrid ABOMC (Kobo), which includes polymethylmethacrylate, butyl methoxydibenzoylmethane, and ethylhexyl methoxycinnamate.

Vitamins

The compositions of the present invention may comprise from about 0.0001% to about 50%, alternatively from about 0.001% to about 10%, and alternatively from about 0.01% to about 5%, of one or more vitamins. Herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, nia-cinnicotinic acid, tocopheryl nicotinate, C1-C18 nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition comprises a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

Peptides and Peptide Derivatives

The compositions of the present invention may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EE-MQRR; Argireline®), and Cu-histidine-glycine-glycine (Cu-HGG, also known as IAMIN®).

The compositions may comprise from about $1 \times 10^{-7}\%$ to about 20%, alternatively from about $1 \times 10^{-6}\%$ to about 10%, and alternatively from about $1 \times 10^{-5}\%$ to about 5% of the peptide.

Sugar Amines

The compositions of the present invention may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Sugar amine compounds useful in the present invention include, for example, N-acetyl-glucosamine, and also those described in PCT Publication WO 02/076423 and U.S. Pat. No. 6,159,485, issued to Yu, et al. In one embodiment, the composition comprises from about 0.01% to about 15%, alternatively from about 0.1% to about 10%, and alternatively from about 0.5% to about 5%, of the sugar amine.

The compositions of the present invention further may comprise non-vitamin antioxidants and radical scavengers, hair growth regulators, flavonoids, minerals, preservatives, phytosterols and/or plant hormones, protease inhibitors, tyrosinase inhibitors, anti-inflammatory agents and N-acyl amino acid compounds.

Suitable non-vitamin antioxidants and radical scavengers include, but are not limited to, BHT (butylated hydroxy toluene), L-ergothioneine (available as THIOTANE™); tetrahydrocurcumin, cetyl pyridinium chloride, carnosine, diethylhexyl syrinylidene malonate (available as OXYNEX™) hexadec-8-ene-1,16-dicarboxylic acid (octadecene dioic acid; ARLATONE™ Dioic DCA from Uniqema), ubiquinone (co-enzyme Q10), tea extracts including green tea extract, yeast extracts or yeast culture fluid (e.g., Pitera®), and combinations thereof.

Suitable hair growth regulators include, but are not limited to, hexamidine, butylated hydroxytoluene (BHT), hexanediol, panthenol and pantothenic acid derivates, their isomers, salts and derivatives, and mixtures thereof.

Suitable minerals include zinc, manganese, magnesium, copper, iron, selenium and other mineral supplements. "Mineral" is understood to include minerals in various oxidation states, mineral complexes, salts, derivatives, and combinations thereof.

Suitable examples of plant sterols (phytosterols) and/or plant hormones include, but are not limited to, sitosterol, stigmasterol, campesterol, brassicasterol, kinetin, zeatin, and mixtures thereof.

Suitable protease inhibitors include, but are not limited to, hexamidine, vanillin acetate, menthyl anthranilate, soybean trypsin inhibitor, Bowman-Birk inhibitor, and mixtures thereof.

Suitable tyrosinase inhibitors include, but are not limited to, sinablanca (mustard seed extract), tetrahydrocurcumin, cetyl pyridinium chloride, and mixtures thereof.

Suitable anti-inflammatory agents include, but are not limited to, glycyrrhizic acid (also known as glycyrrhizin, glycyrrhixinic acid, and glycyrrhetinic acid glycoside), glycyrrhetenic acid, other licorice extracts, and combinations thereof.

Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradename SEPIWHITE® from Seppic (France).

Other useful skin care actives include moisturizing and/or conditioning agents, such as glycerol, petrolatum, caffeine, and urea; yeast extracts (for example, Pitera™); dehydroepiandrosterone (DHEA), its analogs and derivatives; exfoliating agents, including alpha- and beta-hydroxyacids, alpha-keto acids, glycolic acid and octanoyl salicylate; antimicrobial agents; antidandruff agents such as piroctone olamine, 3,4,4'-trichlorocarbanilide (trichlosan), triclocarban and zinc pyrithione; dimethyl aminoethanol (DMAE); creatine; skin lightening agents such as kojic acid, mulberry extract, hydroquinone, arbutin, and deoxy-arbutin; (sunless) tanning agents, such as dihydroxy acetone (DHA); isomers, salts, and derivatives of any of the foregoing; and mixtures thereof.

Humectants

The compositions of the present invention may include one or more humectants. The composition of the present invention may comprise from about 1% to about 30%; alternatively, from about 2% to about 20%; or, alternatively, from about 3% to about 15% of the humectant, when present. An exemplary class of humectants is polyhydric alcohols. Suitable polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; hexylene glycol; butylene glycol (e.g., 1,3-butylene glycol); pentylene glycol; hexane triol (e.g., 1,2,6-hexanetriol); glycerine; ethoxylated glycerine; and propoxylated glycerine.

Other suitable humectants include sodium 2-pyrrolidone-5-carboxylate, guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; panthenol; sodium pyroglutamate (NaPCA), water-soluble glyceryl poly(meth)acrylate lubricants (such as Hispagel®) and mixtures thereof.

Colorants

The composition of the present invention may comprise from about 0.00001% to about 25%, and alternatively from about 0.01% to about 10%, of a colorant. Non-limiting classes of suitable colorants include, but are not limited to organic and/or inorganic pigments, natural and/or synthetic dyes, lakes, including FD&C and/or D&C lakes and blends, and mixtures of any of the foregoing.

Non-limiting examples of suitable colorants include iron oxides, ferric ammonium ferrocyanide, manganese violet, ultramarine blue, and chromium oxide, phthalocyanine blue and green pigment, encapsulated dyes, inorganic white pigments, for example $TiO_2$, $ZnO$, or $ZrO_2$, FD&C dyes, D&C dyes, and mixtures thereof.

Oil Control Agents

The compositions of the present invention may comprise one or more compounds useful for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof. The compositions may comprise from about 0.0001% to about 15%, alternatively from about 0.01% to about 10%, alternatively from about 0.1% to about 5%, and alternatively from about 0.2% to about 2%, of an oil control agent.

EXAMPLES

The following examples of the compositions according to the present invention are prepared by first combining the water phase ingredients and heating to 80° C. while mixing. Next, the oil phase ingredients are separately combined and heated to 80° C. while mixing. The oil phase is then added to the water phase and the resulting emulsion is milled using a rotor stator mill. The thickener phase is next prepared by mixing the ingredients, and this thickener phase is then added to the emulsion and the emulsion is cooled while mixing. When the composition reaches 55° C. the remaining ingredients are added and the composition is mixed until uniform while maintaining the composition at 55° C. The composition is then poured into suitable containers.

Examples 1-5

|  | Example 1 | Example 2 | Example 3 | Example 4 | Example 5 |
|---|---|---|---|---|---|
| Water Phase: | | | | | |
| Water | qs | qs | qs | qs | qs |
| Glycerin | — | 2.0 | — | — | 5.0 |
| Dipropylene Glycol | — | — | 1.0 | — | — |
| Butylene Glycol | — | — | 2.0 | — | 1.0 |
| Disodium EDTA | 0.05 | 0.05 | 0.05 | 0.05 | 0.05 |
| Carnosine | — | 0.01 | — | — | — |
| Phenoxyethanol | 0.375 | 0.375 | 0.375 | 0.375 | 0.375 |
| Niacinamide | — | 2.0 | — | — | 1.0 |
| D-panthenol | — | 0.5 | — | — | 0.15 |
| N-acetyl glucosamine | — | 0.5 | — | — | — |
| Aloe Vera Gel | — | 1.0 | — | — | — |
| Green Tea Extract | — | 0.2 | — | — | — |
| Oil Phase: | | | | | |
| Isopropyl isostearate | 0.5 | 0.5 | — | 0.5 | — |
| Isohexadecane | 1.5 | 1.5 | 3.0 | 1.5 | — |
| Dow Corning 2503[1] | 10.0 | 10.0 | 10.0 | 10.0 | 10.0 |
| Cetyl Palmitate | — | — | 3.0 | — | — |
| Cirebelle 303[2] | — | — | — | 3.0 | — |
| Shea Butter | — | — | 2.0 | — | — |
| Petrolatum | — | — | — | — | 4.0 |
| Cetyl Alcohol | 1.2 | 1.2 | 1.2 | 1.2 | 1.2 |
| Stearyl Alcohol | 1.2 | 1.2 | 1.2 | 1.2 | 1.2 |
| Cetearyl Glucoside and Cetearyl Alcohol | 0.2 | 0.2 | 0.2 | 0.2 | 0.2 |
| PEG-100 Stearate | 0.1 | 0.1 | 0.1 | 0.1 | 0.1 |
| Stearic Acid | 0.1 | 0.1 | 0.1 | 0.1 | 0.1 |
| Thickener Phase: | | | | | |
| Symdiol 68[3] | 0.8 | 0.8 | 0.8 | 0.8 | 0.8 |
| Xanthan gum | — | — | — | 0.1 | — |
| Makimousse-12[4] | 0.6 | 0.6 | 0.3 | 0.4 | 0.3 |
| Makimousse-25[5] | — | — | 0.2 | — | — |
| AquaKeep 10SH-NF[6] | — | — | — | — | 0.3 |
| Particulate Material: | | | | | |
| Tapioca Pure[7] | — | — | 6.0 | — | 3.0 |
| Dry Flo TS[8] | 10.0 | 10.0 | 6.0 | — | 10.0 |
| KSP 100[9] | — | — | — | 10.0 | — |
| Additional Ingredients: | | | | | |
| Fragrance | — | 0.1 | — | — | — |
| FD&C Blue #1 | — | 0.0001 | — | — | — |
| KTZ Interfine Red[10] | — | — | — | 1.0 | — |
| Total: | 100% | 100% | 100% | 100% | 100% |
| Wax Level | 12.4% | 12.4% | 17.4% | 15.4% | 16.4% |
| Oil Level | 2.0% | 2.0% | 3.0% | 2.0% | 0% |
| Wax to Oil Ratio | 6.2 | 6.2 | 5.8 | 7.7 | NA |

[1]Stearyl dimethicone and octadecene, from Dow Corning
[2]Synthetic wax, from Arch Chemicals, Inc.
[3]1,2-hexanediol and caprylyl glycol, from Symrise
[4]Sodium polyacrylate starch, from Kobo Products Inc.
[5]Sodium polyacrylate starch, from Kobo Products Inc.
[6]Sodium acrylate crosspolymer-2, from Kobo Products, Inc.
[7]Tapioca starch, from Akzo Nobel
[8]Tapioca starch and polymethylsilsesquioxane, from Akzo Nobel
[9]Vinyl dimethicone/methicone silsesquioxane crosspolymer, from Shin Etsu
[10]Titanium dioxide coated mica, from Kobo Products, Inc.

Examples 6-10

|  | Example 6 | Example 7 | Example 8 | Example 9 | Example 10 |
|---|---|---|---|---|---|
| Water Phase: | | | | | |
| Water | qs | qs | qs | qs | qs |
| Glycerin | — | 2.0 | 2.0 | — | — |
| Dipropylene Glycol | — | — | 1.0 | — | — |
| Butylene Glycol | — | — | 2.0 | — | 1.0 |
| Disodium EDTA | 0.05 | 0.05 | 0.05 | 0.05 | 0.05 |
| Carnosine | — | 0.01 | — | — | — |
| Phenoxyethanol | 0.375 | 0.375 | 0.375 | 0.375 | 0.375 |
| Niacinamide | — | 2.0 | 5.0 | — | 1.0 |
| D-panthenol | — | 0.5 | 0.5 | — | 0.15 |
| N-acetyl glucosamine | — | 0.5 | — | — | — |
| Aloe Vera Gel | — | 1.0 | — | 2.0 | — |
| Green Tea Extract | — | 0.2 | — | — | 1.0 |
| Oil Phase: | | | | | |
| Isopropyl isostearate | 0.5 | 0.5 | 0.5 | 1.0 | — |
| Isohexadecane | 0.5 | 1.5 | 1.5 | 2.5 | — |
| Dow Corning 2503[1] | — | — | 10.0 | — | 20.0 |
| Dow Corning 580[10] | — | — | — | 14.0 | — |
| Cetyl Palmitate | 6.0 | 8.0 | — | — | — |
| Cirebelle 303[2] | — | — | — | — | — |
| Shea Butter | — | 2.0 | — | — | 3.0 |
| Petrolatum | 2.0 | — | — | — | 2.0 |
| Cetyl Alcohol | 1.2 | 1.2 | 2.4 | 0.8 | 1.2 |
| Stearyl Alcohol | 1.2 | 1.2 | 2.4 | 0.8 | 1.2 |
| Behenyl Alcohol | — | — | — | 0.8 | — |
| Cetearyl Glucoside and Cetearyl Alcohol | 0.2 | 0.2 | 0.2 | 0.2 | 0.2 |
| PEG-100 Stearate | 0.1 | 0.1 | 0.1 | 0.1 | 0.1 |
| Stearic Acid | 0.1 | 0.1 | 0.1 | 0.1 | 0.1 |
| Thickener Phase: | | | | | |
| Symdiol 68[3] | 0.8 | 0.8 | 0.8 | 0.8 | 0.8 |
| Xanthan gum | — | — | — | — | 0.1 |
| Makimousse-12[4] | 0.6 | 0.6 | — | 0.5 | — |
| Makimousse-25[5] | — | — | 0.5 | — | — |
| AquaKeep 10SH-NF[6] | — | — | — | — | 0.5 |
| Particulate Material: | | | | | |
| Tapioca Pure[7] | — | — | 6.0 | — | — |
| Dry Flo TS[8] | 10.0 | 10.0 | 6.0 | 8.0 | 15.0 |
| KSP 100[9] | — | — | — | 5.0 | — |
| Total: | 100% | 100% | 100% | 100% | 100% |
| Wax Level | 10.4% | 12.4% | 14.8% | 16.4% | 27.4% |
| Oil Level | 1.0% | 2.0% | 2.0% | 3.5% | 0% |
| Wax to Oil Ratio | 10.4 | 6.2 | 7.4 | 4.7 | NA |

[1]Stearyl dimethicone and octadecene, from Dow Corning
[2]Synthetic wax, from Arch Chemicals, Inc.
[3]1,2-hexanediol and caprylyl glycol, from Symrise
[4]Sodium polyacrylate starch, from Kobo Products Inc.
[5]Sodium polyacrylate starch, from Kobo Products Inc.
[6]Sodium acrylate crosspolymer-2, from Kobo Products, Inc.
[7]Tapioca starch, from Akzo Nobel
[8]Tapioca starch and polymethylsilsesquioxane, from Akzo Nobel
[9]Vinyl dimethicone/methicone silsesquioxane crosspolymer, from Shin Etsu
[10]Stearoxy trimethylsilane and stearyl alcohol, from Dow Corning

Comparative Example A

|  | Comparative Example A |
|---|---|
| Water Phase: | |
| Water | qs |
| Disodium EDTA | 0.05 |
| Phenoxyethanol | 0.375 |

-continued

|  | Comparative Example A |
|---|---|
| Oil Phase: | |
| Isopropyl isostearate | 0.5 |
| Isohexadecane | 1.5 |
| Dow Corning 2503[1] | 10.0 |
| Cetyl Alcohol | 1.2 |
| Stearyl Alcohol | 1.2 |
| Cetearyl Glucoside and Cetearyl Alcohol | 0.2 |
| PEG-100 Stearate | 0.1 |
| Stearic Acid | 0.1 |
| Thickener Phase: | |
| Symdiol 68[2] | 0.8 |
| Makimousse-12[3] | 0.6 |
| Particulate Material: | |
| Dry Flo TS[4] | — |
| Total: | 100% |

[1]Stearyl dimethicone and octadecene, from Dow Corning
[2]1,2-hexanediol and caprylyl glycol, from Symrise
[3]Sodium polyacrylate starch, from Kobo Products Inc.
[4]Tapioca starch and polymethylsilsesquioxane, from Akzo Nobel The compositions in Example 1 and Comparative Example A were tested and evaluated by an expert sensory panel. These two formulations are identical except that example 1 contains 10% Dry Flo TS, a tapioca starch coated with polymethylsilsesquioxane from Akzo Nobel, in place of 10% of the water in Comparative Example A. For this testing, 0.1 grams of a product was applied to the volar forearm and various rub-in and after feel attributes such as consistency, spreading, absorption, stickiness, smoothness and coating level were assessed by a panel of 2 sensory experts.

The results of this sensory comparison are summarized in the table below, and show that the addition of the 10% Dry Flo TS particulate material resulted in faster absorption, reduced stickiness, reduced drag, and reduced coating level, but the creamy product consistency upon application was maintained.

| Evaluation Time | Attribute | Comparative Example A (With No Particulate Material) | Example 1 (With 10% Dry Flo TS Particulate Material) |
|---|---|---|---|
| Rub In/ Application | Consistency | very creamy | very creamy |
|  | Spreading | OK | OK to good |
|  | Absorption | OK | good/fast |
| 2 Minutes On Skin | Stickiness | moderate | low |
|  | Smoothness | high drag | some drag |
| 6 Minutes on Skin | Stickiness | moderate | very slight |
|  | Smoothness | some drag | slight drag |
|  | Coating Level | slightly more than moderate coating | slightly more than low coating |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A body butter composition, comprising:
   a) an oil phase mixture comprising:
      (i) from about 5% to about 30% by weight of the composition, of a wax material; and
      (ii) from about 1% to about 20% by weight of the composition, of an oil that is liquid at room temperature;
      the oil phase mixture having a melting point of about 25° C. to about 50° C.;
   b) a water phase comprising:
      (i) from about 0.1% to about 5%, by weight of the composition, of a superabsorbent polymer, wherein said superabsorbent polymer can, in its dry state, absorb at least 20 times its weight of aqueous fluid; and
      (ii) from about 20% to about 80% by weight of the composition, of water; and
   c) from about 8% to about 25%, by weight of the composition, of non-crosslinked starch particles;
   wherein the composition is an oil in water emulsion; the composition has a viscosity at 25° C. of about 100,000 cP to about 2,000,000 cP; the ratio of wax material to oil is from about 2:1 to about 20:1, and wherein oil phase mixture has a melting point of about 28° C. to about 40° C.

2. The composition of claim 1 wherein the ratio of wax material to oil is from about 3:1 to about 10:1.

3. The composition of claim 1, wherein the viscosity at 25° C. is about 200,000 cP to about 1,000,000 cP.

4. The composition of claim 1, wherein the oil phase mixture is from about 6% to about 40%, by weight of the composition.

5. The composition of claim 1, wherein the starch particles are substantially spherical particles.

6. The composition of claim 5, wherein the starch particles are selected from the group consisting of tapioca starch, corn starch, potato starch, glyceryl starch, aluminum starch octenylsuccinate, calcium starch octenylsuccinate, polymethylsilsesquioxane coated tapioca starch, and combinations thereof.

7. The composition of claim 5, wherein the starch particles have a weight-average particle size of from 5 to 30 microns.

8. The composition of claim 1, wherein the starch particles comprise substantially spherical particles in an amount of from about 10% to about 16% by weight of the composition.

9. The composition of claim 1, wherein the superabsorbent polymer is selected from the group consisting of sodium polyacrylate, sodium polacrylate starch, sodium acrylates crosspolymer-2 and mixtures thereof.

10. The composition of claim 1, wherein the superabsorbent polymer is in the form of irregular or non-spherical particles.

11. The composition of claim 1, wherein the superabsorbent polymer, once hydrated, comprises particles having a weight-average particle size from about 10 µm to about 300 µm.

12. The composition of claim 11, wherein the superabsorbent polymer, once hydrated, comprises particles having a weight-average particle size from about 20 µm to about 200 µm.

13. The composition of claim 1, further comprising from about 1% to about 40%, by weight, of a UV active.

14. The composition of claim 1, further comprising an active or agent selected from a group consisting of sugar amines, vitamins, oil control agents, humectants, emollients, phytosterols, hexamidine compounds, tightening agents, anti-wrinkle actives, anti-atrophy actives, flavonoids, N-acyl amino acid compounds, retinoids, peptides, particulate materials, anti-cellulite agents, desquamation actives, anti-acne actives, anti-oxidants, radical scavengers, conditioning agents, anti-inflammatory agents, tanning actives, skin lightening agents, botanical extracts, antimicrobial actives, anti-fungal actives, antibacterial actives, antiperspirant actives, sensates, preservatives, anti-dandruff actives, substantivity polymers, detersive surfactants, and combinations thereof.

15. The composition of claim 14, wherein the actives are vitamins that are selected from the group consisting of vitamin B3 compound, ascorbic acid, tocopherol acetate, panthenol, dexpanthenol, magnesium ascorbyl phosphate, sodium ascorbyl phosphate, retinyl propionate, and combinations thereof.

16. A body butter composition, comprising:
  a) an oil phase mixture comprising:
    (i) from about 5% to about 30% by weight of the composition, of a wax material; and
    (ii) optionally from about 1% to about 20% by weight of the composition, of an oil that is liquid at room temperature;
    the oil phase mixture having a melting point of about 25° C. to about 50° C.;
  b) a water phase comprising:
    (i) from about 0.1% to about 5%, by weight of the composition, of a superabsorbent polymer, wherein said superabsorbent polymer can, in its dry state, absorb at least 20 times its weight of aqueous fluid; and
    (ii) from about 20% to about 85% by weight of the composition of water; and
  c) from about 6% to about 30%, by weight of the composition, of particulate material selected from the group consisting of starch particles, silicone elastomer particles and combinations thereof;
  wherein the composition is an oil in water emulsion.

17. The composition of claim 16, further comprising a ratio of wax material to oil from about 2:1 to about 20:1.

18. The composition of claim 17, wherein the ratio of wax material to oil is from about 3:1 to about 10:1.

19. The composition of claim 16, wherein the composition has a viscosity at 25° C. of about 100,000 cP to about 2,000,000 cP.

20. The composition of claim 19, wherein the viscosity at 25° C. is about 200,000 cP to about 1,000,000 cP.

21. The composition of claim 16, wherein oil phase mixture has a melting point of about 28° C. to about 40° C.

22. The composition of claim 16, wherein the oil phase mixture is from about 6% to about 40%, by weight, of the composition.

23. The composition of claim 16, wherein the particulate material is substantially spherical particles.

24. The composition of claim 23, wherein the composition comprises from about 8% to about 25%, by weight of the composition of the particulate material.

25. The composition of claim 23, wherein the particulate material is selected from the group consisting of tapioca starch, corn starch, potato starch, glyceryl starch, aluminum starch octenylsuccinate, calcium starch octenylsuccinate, polymethylsilsesquioxane coated tapioca starch, and combinations thereof.

26. The composition of claim 23, wherein the substantially spherical particles have a weight-average particle size of from 5 to 30 microns.

27. The composition of claim 16, wherein the particulate material is non-crosslinked starch particles.

28. The composition of claim 16, wherein the superabsorbent polymer is selected from the group consisting of sodium polyacrylate, sodium polacrylate starch, sodium acrylates crosspolymer-2 and mixtures thereof.

29. The composition of claim 16, wherein the superabsorbent polymer is in the form of irregular of non-spherical particles.

30. The composition of claim 16, wherein the superabsorbent polymer, once hydrated, comprises particles having a weight-average particle size from about 10 µm to about 300 µm.

31. The composition of claim 30, wherein the superabsorbent polymer, once hydrated, comprises particles having a weight-average particle size from about 20 µm to about 200 µm.

32. The composition of claim 16, further comprising from about 1% to about 40%, by weight, of a UV active.

33. The composition of claim 16, further comprising an active or agent selected from a group consisting of sugar amines, vitamins, oil control agents, humectants, emollients, phytosterols, hexamidine compounds, tightening agents, anti-wrinkle actives, anti-atrophy actives, flavonoids, N-acyl amino acid compounds, retinoids, peptides, particulate materials, anti-cellulite agents, desquamation actives, anti-acne actives, anti-oxidants, radical scavengers, conditioning agents, anti-inflammatory agents, tanning actives, skin lightening agents, botanical extracts, antimicrobial actives, anti-fungal actives, antibacterial actives, antiperspirant actives, sensates, preservatives, anti-dandruff actives, substantivity polymers, detersive surfactants, and combinations thereof.

* * * * *